(12) United States Patent
Wood et al.

(10) Patent No.: US 12,383,709 B2
(45) Date of Patent: *Aug. 12, 2025

(54) BILIARY ACCESS CATHETER SYSTEM AND METHODS FOR ACCESSING THE BILIARY TREE

(71) Applicant: BOSTON SCIENTIFIC SCIMED, INC., Maple Grove, MN (US)

(72) Inventors: Mark D. Wood, Shrewsbury, MA (US); John Deane, Salem, NH (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 533 days.

This patent is subject to a terminal disclaimer.

(21) Appl. No.: 17/152,546

(22) Filed: Jan. 19, 2021

(65) Prior Publication Data

US 2021/0162182 A1    Jun. 3, 2021

Related U.S. Application Data

(62) Division of application No. 15/040,943, filed on Feb. 10, 2016, now Pat. No. 10,905,859, which is a (Continued)

(51) Int. Cl.
*A61M 25/00* (2006.01)
*A61M 25/01* (2006.01)
(Continued)

(52) U.S. Cl.
CPC ........ *A61M 25/09* (2013.01); *A61M 25/0023* (2013.01); *A61M 25/01* (2013.01);
(Continued)

(58) Field of Classification Search
CPC .......... A61M 25/0169; A61M 25/0172; A61M 2025/0177; A61M 2025/018;
(Continued)

(56) References Cited

U.S. PATENT DOCUMENTS 5,238,004 A    8/1993 Sahatjian et al.
5,772,609 A    6/1998 Nguyen et al.
(Continued)

*Primary Examiner* — William R Carpenter
(74) *Attorney, Agent, or Firm* — Seager, Tufte & Wickhem, LLP

(57) ABSTRACT

Medical devices and methods are disclosed. An example method for accessing a body lumen may include providing a catheter system. The catheter system may include a catheter shaft having a lumen defined therein and an outer wall surface having a channel formed therein. A first guidewire may be disposed in the channel and a second guidewire may be disposed in the lumen. The method may also include advancing the catheter system through a body lumen to a location where the body lumen splits into a first section and a second section, advancing the first guidewire into the first section, and advancing the second guidewire into the second section, and advancing the catheter shaft along the second guidewire and into the second section. Advancing the catheter shaft along the second guidewire and into the second section may remove at least a portion of the first guidewire from the channel.

18 Claims, 14 Drawing Sheets

Related U.S. Application Data division of application No. 13/727,913, filed on Dec. 27, 2012, now Pat. No. 9,278,198.

(60) Provisional application No. 61/580,979, filed on Dec. 28, 2011.

(51) Int. Cl.
*A61M 25/09* (2006.01)
*A61M 25/10* (2013.01)

(52) U.S. Cl.
CPC ............... *A61M 2025/0183* (2013.01); *A61M 2025/09125* (2013.01); *A61M 2025/1045* (2013.01)

(58) Field of Classification Search
CPC .. A61M 2025/0183; A61M 2025/0188; A61M 25/01; A61M 25/09; A61M 2025/1045
See application file for complete search history.

(56) References Cited

U.S. PATENT DOCUMENTS

| | | | |
|---|---|---|---|
| 6,007,522 A | 12/1999 | Agro et al. | |
| 6,129,738 A | 10/2000 | Lashinski et al. | |
| 6,139,510 A | 10/2000 | Palermo | |
| 6,221,090 B1 | 4/2001 | Wilson | |
| 6,346,093 B1 | 2/2002 | Allman et al. | |
| 6,508,803 B1 | 1/2003 | Horikawa et al. | |
| 6,582,401 B1 | 6/2003 | Windheuser et al. | |
| 7,037,293 B2 | 5/2006 | Carrillo et al. | |
| 7,160,283 B2 | 1/2007 | Richardson et al. | |
| 7,179,252 B2 | 2/2007 | Agro et al. | |
| 7,544,193 B2 | 6/2009 | Agro et al. | |
| 7,632,241 B2 | 12/2009 | Raijman et al. | |
| 7,993,389 B2 | 8/2011 | Globerman | |
| 8,308,793 B2 | 11/2012 | Meyer et al. | |
| 2001/0029396 A1 | 10/2001 | Wilson et al. | |
| 2001/0044622 A1 | 11/2001 | Vardi et al. | |
| 2002/0055732 A1 | 5/2002 | Wilson | |
| 2004/0064128 A1 | 4/2004 | Raijman et al. | |
| 2004/0098085 A1* | 5/2004 | Ricci | A61F 2/95 623/1.11 |
| 2005/0059890 A1 | 3/2005 | Deal et al. | |
| 2006/0100694 A1 | 5/2006 | Globerman | |
| 2006/0293695 A1 | 12/2006 | Ricci et al. | |
| 2007/0250001 A1* | 10/2007 | Hilaire | A61F 2/954 604/103.04 |
| 2008/0027411 A1* | 1/2008 | Von Oepen | A61M 25/0029 600/585 |
| 2011/0137292 A1 | 6/2011 | Richardson et al. | |
| 2012/0239129 A1 | 9/2012 | Mertens et al. | |
| 2013/0158507 A1* | 6/2013 | Brown | A61M 25/0108 604/506 |

\* cited by examiner

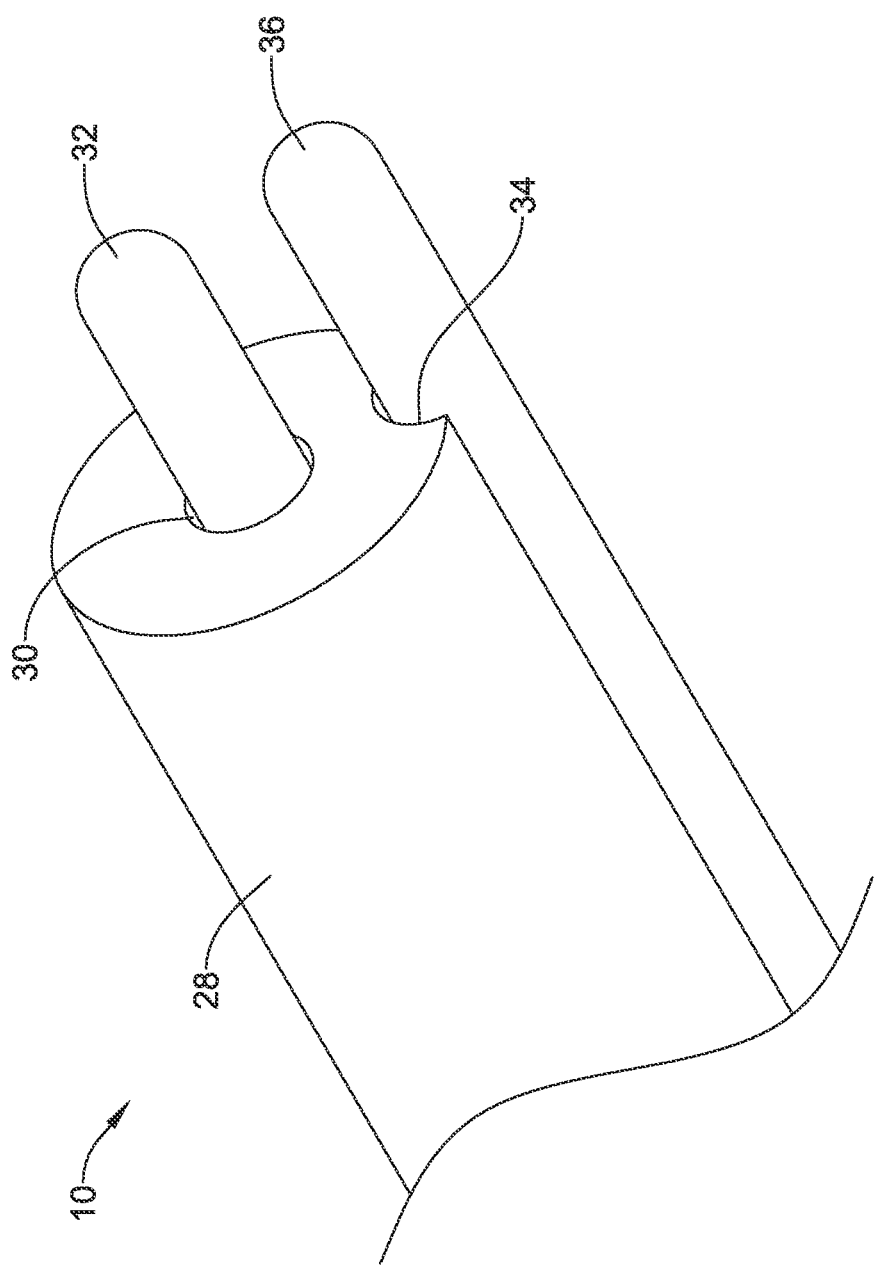

BILIARY ACCESS CATHETER SYSTEM AND METHODS FOR ACCESSING THE BILIARY TREE

CROSS-REFERENCE TO RELATED APPLICATIONS

This application is a continuation of U.S. application Ser. No. 15/040,943, filed Feb. 10, 2016, which is a divisional application of U.S. application Ser. No. 13/727,913, filed Dec. 27, 2012, now U.S. Pat. No. 9,278,198, which claims priority under 35 U.S.C. § 119 to U.S. Provisional Application Ser. No. 61/580,979, filed Dec. 28, 2011, the entirety of which is incorporated herein by reference.

TECHNICAL FIELD

The present invention pertains to medical devices as well as methods for manufacturing and using medical devices. More particularly, the present invention pertains to methods for accessing body lumens along the biliary tree.

BACKGROUND

A wide variety of medical devices have been developed for medical use, for example, endoscopic use. Some of these devices include catheters, catheter systems, endoscopic instruments, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The invention provides design, material, manufacturing method, and use alternatives for medical devices such as catheters, catheter systems, endoscopic instruments, biliary catheters and catheter systems, and the like. Medical devices including devices and systems for endoscopic interventions that may access the biliary tree are disclosed as well as methods for making and using such devices. An example method for accessing a body lumen may include providing a catheter system. The catheter system may include a catheter shaft having a lumen defined therein and an outer wall surface having a channel formed therein. A first guidewire may be disposed in the channel and a second guidewire may be disposed in the lumen. The method may also include advancing the catheter system through a body lumen to a location where the body lumen splits into a first section and a second section, advancing the first guidewire into the first section, advancing the second guidewire into the second section, and advancing the catheter shaft along the second guidewire and into the second section. Advancing the catheter shaft along the second guidewire and into the second section may remove at least a portion of the first guidewire from the channel.

Another example method for accessing a body lumen may include providing a catheter. The catheter may have a guidewire lumen defined therein and an outer wall surface having a channel formed therein. The method may also include disposing a first guidewire in the channel, disposing a second guidewire in the guidewire lumen, advancing the catheter through a body lumen to a location where a common duct splits into a first duct and a second duct, advancing the catheter into the first duct, retracting the catheter from the first duct while leaving the first guidewire in the first duct, and advancing the catheter into the second duct.

An example dual-wire catheter system for accessing a body lumen along the biliary and/or pancreatic tract is also disclosed. The catheter system may include an elongate catheter shaft having a guidewire lumen defined therein and having an outer surface with a guidewire channel formed therein. The guidewire lumen may extend along the entire length of the catheter shaft. The guidewire channel may extend along the full length of the catheter shaft. A first guidewire may be disposed in the guidewire lumen. A second guidewire may be disposed in the guidewire channel.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 2 is a side view of a portion of an example catheter system;

Figure 1:
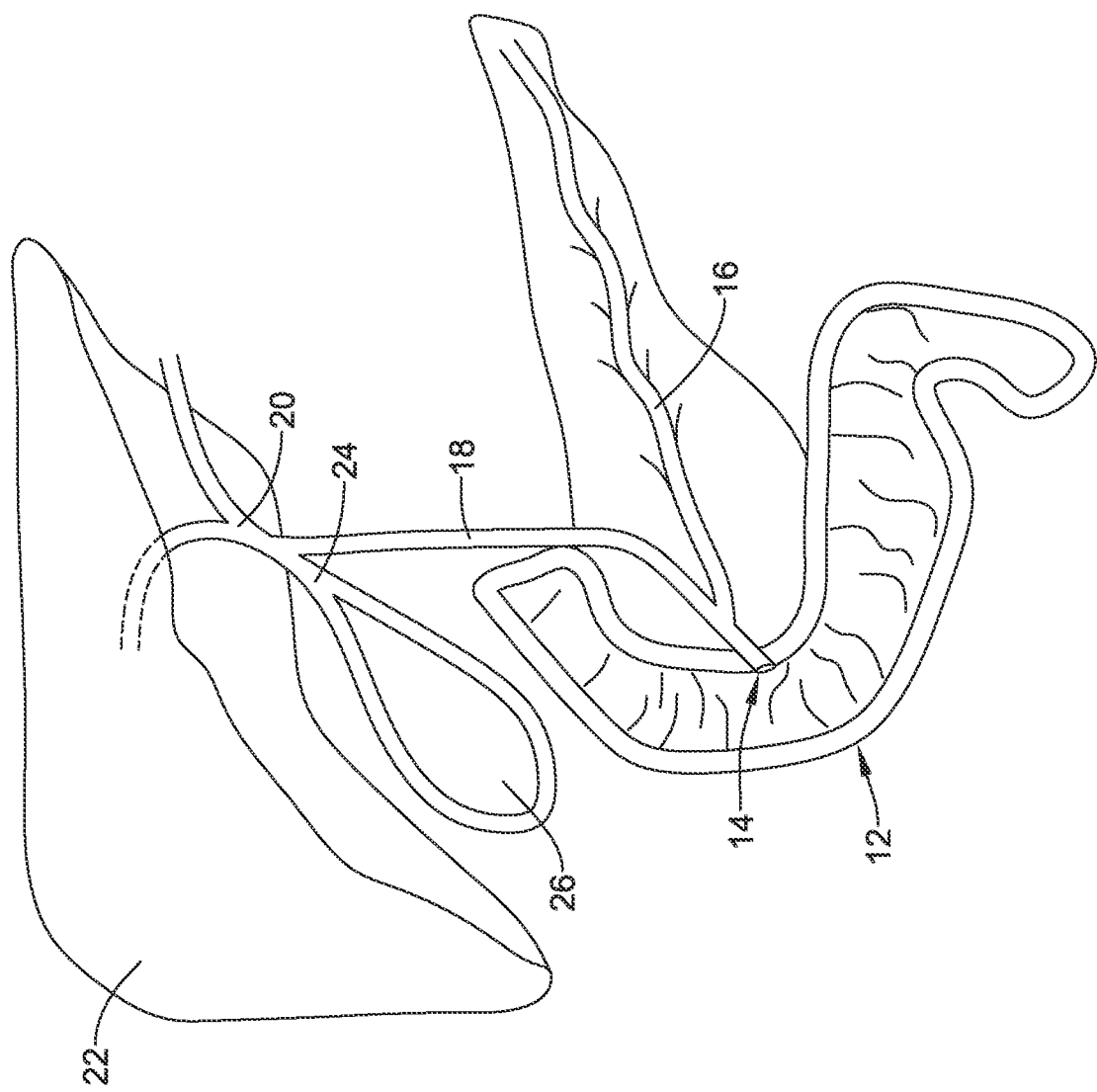
FIG. 1 is an overview of the biliary tree.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Endoscopic retrograde cholangiopancreatography (ERCP) is used primarily to diagnose and treat conditions of the bile ducts including, for example, gallstones, inflammatory strictures, leaks (e.g., from trauma, surgery, etc.), and cancer. Through the endoscope, the physician can see the inside of the stomach and duodenum, and inject dyes into the ducts in the biliary tree and pancreas so they can be seen on x-rays. These procedures may necessitate gaining and keeping access to the biliary duct, which may be technically challenging, may require extensive training and practice to gain proficiency, and may require one or more expensive tools in order to perform.

During an ERCP procedure, a number of steps are typically performed while the patient is often sedated or anaesthetized. For example, an endoscope may be inserted through the mouth, down the esophagus, into the stomach, through the pylorus into the duodenum, to a position at or near the ampulla of Vater (the opening of the common bile duct and pancreatic duct). Due to the shape of the ampulla and the angle at which the common bile and pancreatic ducts meet the wall of the duodenum, the distal end of the endoscope is generally placed just past the ampulla. Due to the positioning of the endoscope beyond the ampulla, the endoscopes used in these procedures are usually side-viewing endoscopes. The side-viewing feature provides imaging along the lateral aspect of the tip rather than from the end of the endoscope. This allows the clinician to obtain an image of the medial wall of the duodenum, where the ampulla of Vater is located, even though the distal tip of the endoscope is beyond the opening.

FIG. 1 provides an overview of the biliary system or tree. Illustrated is a portion of the duodenum 12 where the ampulla of Vater 14 is located. For the purposes of this disclosure, the ampulla of Vater 14 is understood to be the same anatomical structure as the papilla of Vater. The ampulla of Vater 14 generally forms the opening where the pancreatic duct 16 and the bile duct 18 can empty into the duodenum 12. The hepatic ducts, generally bearing reference number 20, are connected to the liver 22 and empty into the bile duct 18. Likewise, the cystic duct 24, which is connected to the gall bladder 26, also empties into the bile duct 18. In general, an endoscopic or biliary procedure may include advancing a medical device to a suitable location along the biliary tree and then performing the appropriate intervention.

Accessing a target along the biliary tree may often involve advancing an endoscope through the duodenum 12 to a position adjacent to the ampulla of Vater 14 and advancing a catheter through the endoscope and through the ampulla of Vater 14 to the intended target. The intended target may be, for example, the common bile duct 18 or the pancreatic duct 16. Because the biliary tree may split into the common bile duct 18 and the pancreatic duct 16 just beyond the ampulla 14, the clinician may advance the catheter through the ampulla 14 and then attempt to advance a guidewire into the intended target duct. Sometimes, however, the clinician may end up inadvertently advancing the guidewire (and/or catheter) into the wrong target. When this happens, the clinician may remove the guidewire and then simply try again. Alternatively, the clinician may choose to pull the catheter from the body while leaving the guidewire in the "undesired" target and then replace the catheter (or advance a new catheter) and load a second guidewire through the catheter to access the "desired" duct. Such a technique may improve the chances of accessing the desired duct, for example, because the initial guidewire may partially block the "undesired" duct. Each of these procedures, however, may include removal of the catheter from the biliary tree and subsequent steps may involve re-cannulation of the ampulla of Vater 14. This may pose technical challenges. In addition, repeated cannulation of, for example, the common bile duct 18 and/or the pancreatic duct 16 may cause undesired side effects.

Disclosed herein are example catheter systems and methods that may improve access to target locations along the biliary tree. In general, these systems and methods may allow a catheter, guidewire, or the like to successfully access a target location along the biliary tree (e.g., the common bile duct 18 and/or the pancreatic duct 16). Furthermore, the systems and methods may allow a clinician to access a target location without having to re-cannulate the ampulla of Vater 14, the common bile duct 18, and/or the pancreatic duct 16.

FIG. 2 illustrates a portion of an example catheter system 10. System 10 may include a catheter shaft 28. Catheter shaft 28, which is shown schematically in FIG. 2, may include a number of features and characteristics commonly associated with catheters as well as other features. For example, a lumen 30 may be formed in catheter shaft 28. Lumen 30 may be a guidewire lumen that is configured to have a first guidewire 32 extend therethrough. In at least some embodiments, lumen 30 extends along the full length of catheter shaft 28. In other embodiments, lumen 30 may extend along only a portion of the length of catheter shaft 28. The distal end or tip of catheter shaft 28 may be rounded, tapered, stepped, enlarged or bulbous in shape, or otherwise configured to be atraumatic.

Catheter shaft 28 may also include a secondary guidewire holding structure 34 that is configured to hold or otherwise house a second guidewire 36. For example, structure 34 may take the form of a channel 34 that may be formed in an outer wall surface of catheter shaft 28. In at least some embodiments, channel 34 is a C-shaped channel that is configured to hold second guidewire 36 therein. When the second guidewire 36 is disposed within and parallel with the channel 34, the second guidewire 36 may be configured to extend radially outward of and beyond the catheter shaft 28, as shown in FIG. 2. In at least some embodiments, a C-shaped channel may be understood to be a channel that is mostly closed or partly open. In some of these and in other embodiments, a C-shaped channel may be defined by a line of weakness or perforation in catheter shaft 28 that can be open (e.g., torn open). In other embodiments, secondary guidewire holding structure 34 may be a guidewire holding tube, a clip or band configured to hold guidewire 36, a tube disposed along catheter shaft 28, or the like, or any other suitable holding structure. These are just examples. Essentially any shape and/or geometry may be utilized for channel 34. For example, channel 34 may have a U- shape.

Figure 2A:
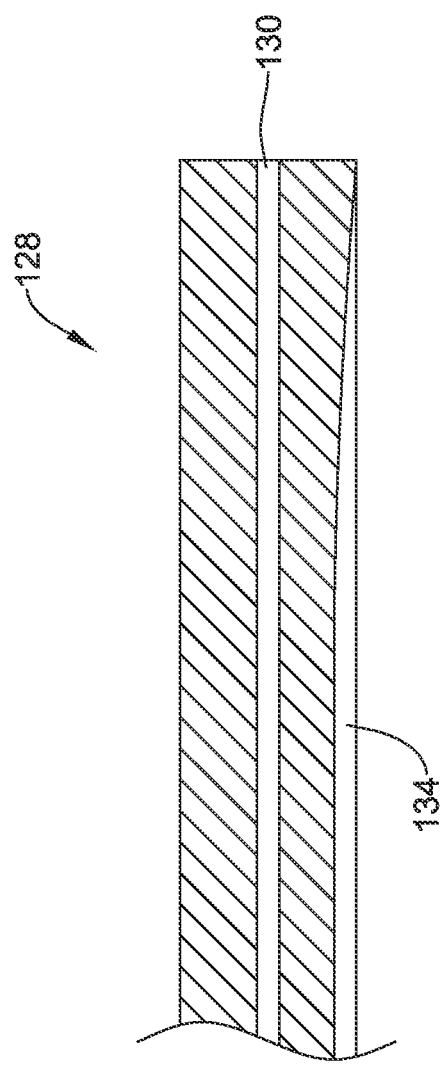
FIG. 2A is a cross-sectional side view of a portion of another example catheter system.

Just like lumen 30, channel 34 may extend along the full length of catheter shaft 28 or along only a portion of catheter shaft 28. In instances where the channel 34 extends along the full length of the catheter shaft 28, the second guidewire 36 may be configured to extend radially outward relative to the catheter shaft 28 along the full length of the catheter shaft 28 (e.g., see also, for example, FIGS. 3-10, which depicts a blackened line representing the second guidewire 36 extending along the full length of the catheter shaft 28). In other instances, channel 34 may terminate at a position proximal of the distal end of catheter shaft 28. This may help to direct guidewire 36 radially outward relative to catheter shaft 28 at the distal end of catheter shaft 28 (and/or divert guidewire 36 from guidewire 32). In some of these and in other embodiments, channel 34 may be distally taper (e.g., reduce) in depth. For example, FIG. 2A illustrates catheter shaft 128 that includes channel 134 that distally tapers in depth. This may divert or direct guidewire 36 radially outward relative to catheter shaft 128 (and/or divert guidewire 36 from guidewire 32). Catheter shaft 128 may or may not include guidewire lumen 130.

Figure 2B:
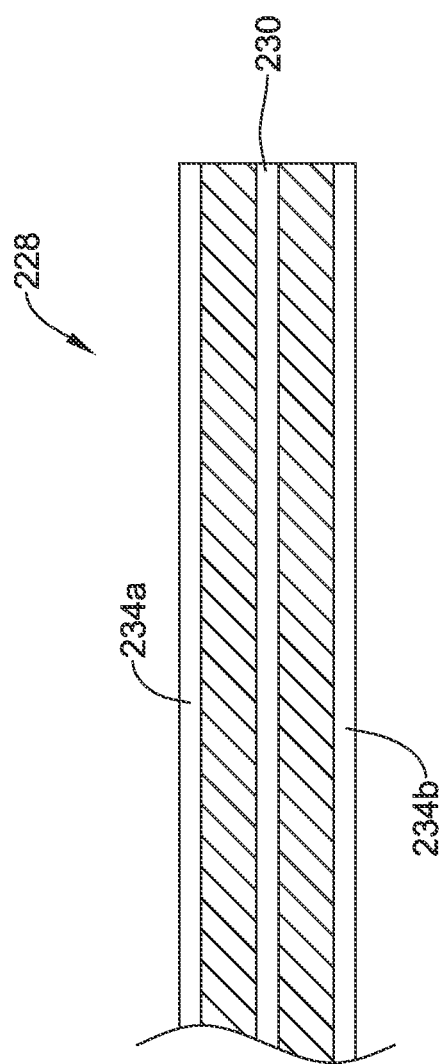
FIG. 2B is a cross-sectional side view of a portion of another example catheter system.

In at least some embodiments, catheter shaft 28 may include additional guidewire holding structure(s) such as, for example, one or more additional C-shaped channels (e.g., resembling channel 34). For example, FIG. 2B illustrates catheter shaft 228 having a first channel 234a (e.g., a first C-shaped channel 234a) and a second channel 234b (e.g., a second C-shaped channel 234b). Catheter shaft 228 may or may not include guidewire lumen 230.

Figure 2C:
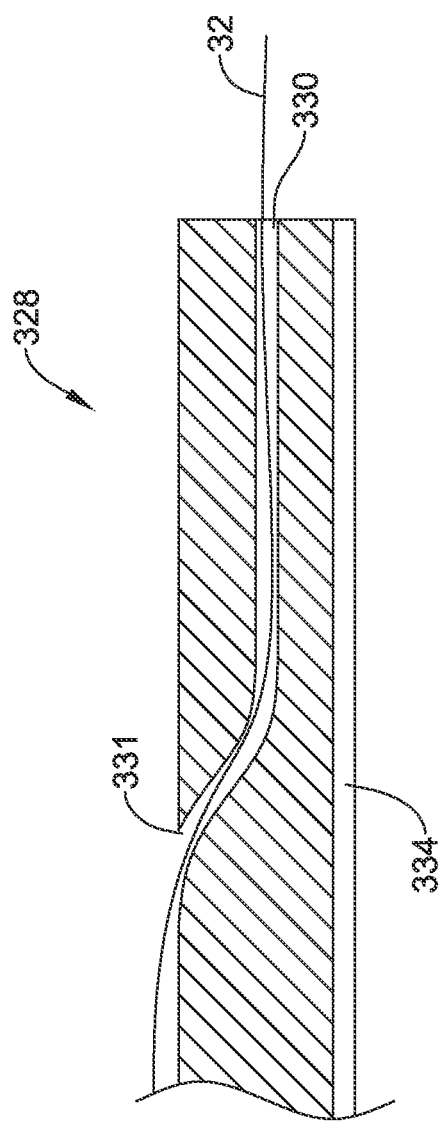
FIG. 2C is a cross-sectional side view of a portion of another example catheter system.
Figure 2D:
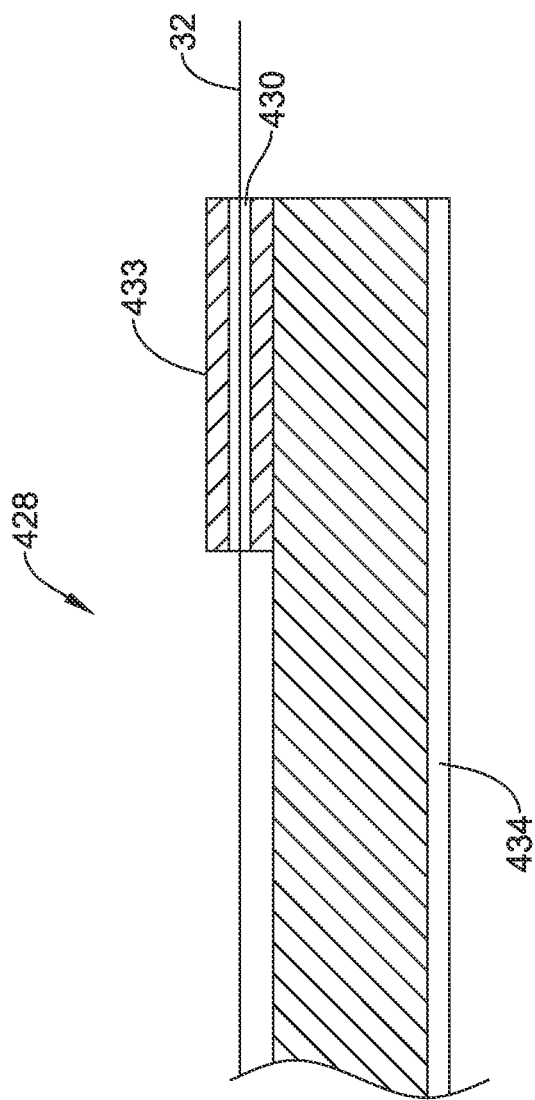
FIG. 2D is a cross-sectional side view of a portion of another example catheter system.

As indicated above, guidewire lumen 30 may extend along the full length of catheter shaft 28. However, this is not intended to be limiting. For example, FIG. 2C illustrates catheter shaft 328 that includes guidewire lumen 330 extending along only a portion of catheter shaft 328 and exiting through the wall of catheter shaft 328 at a guidewire port 331. Catheter shaft 328 may or may not include channel 334 (e.g., C-shaped channel 334). Catheter shaft 328 may be described as a single-operator-exchange or rapid-exchange catheter shaft 328. Other single-operator-exchange or rapid-exchange catheter shafts are contemplated. For example, FIG. 2D illustrates catheter shaft 428, which includes a tubular member 433 having a guidewire lumen 430 defined therein. Tubular member 433 may extend along a portion of the length of catheter shaft 428 (e.g., along an outer surface of catheter shaft 428). Catheter shaft 428 may or may not include channel 434 (e.g., C-shaped channel 434).

FIGS. 3-7 illustrate an example method for using catheter system 10 to access a target duct along the biliary tree. In these examples, the intended target is the common bile duct 18 and the "unintended" target is the pancreatic duct 16. However, this is merely illustrative and may be reversed without departing from the spirit of the disclosure.

Figure 3:
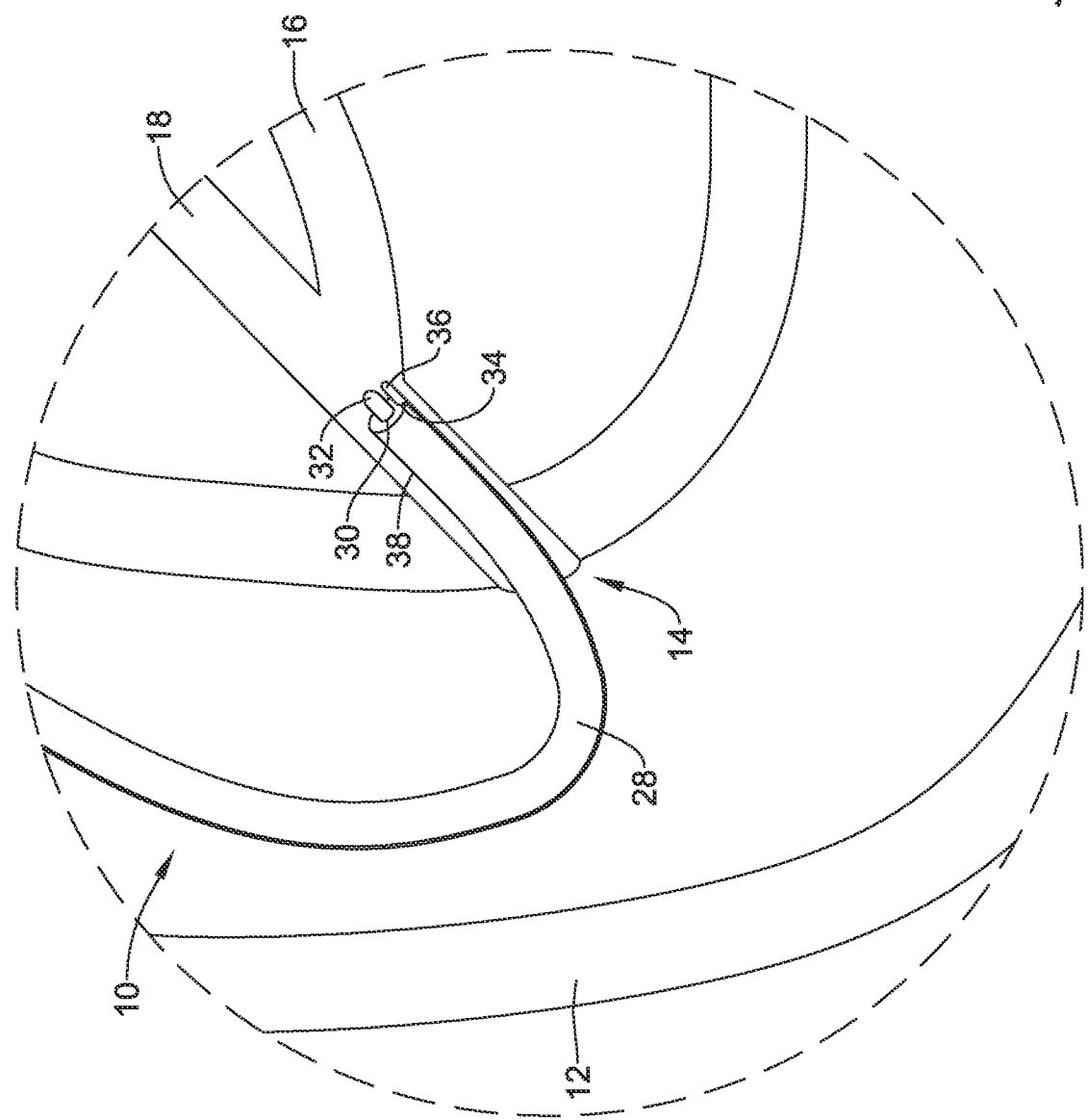
FIGS. 3-7 illustrate an example method for using the example catheter system shown in FIG. 2 to access a target duct along the biliary tree.
Figure 4:
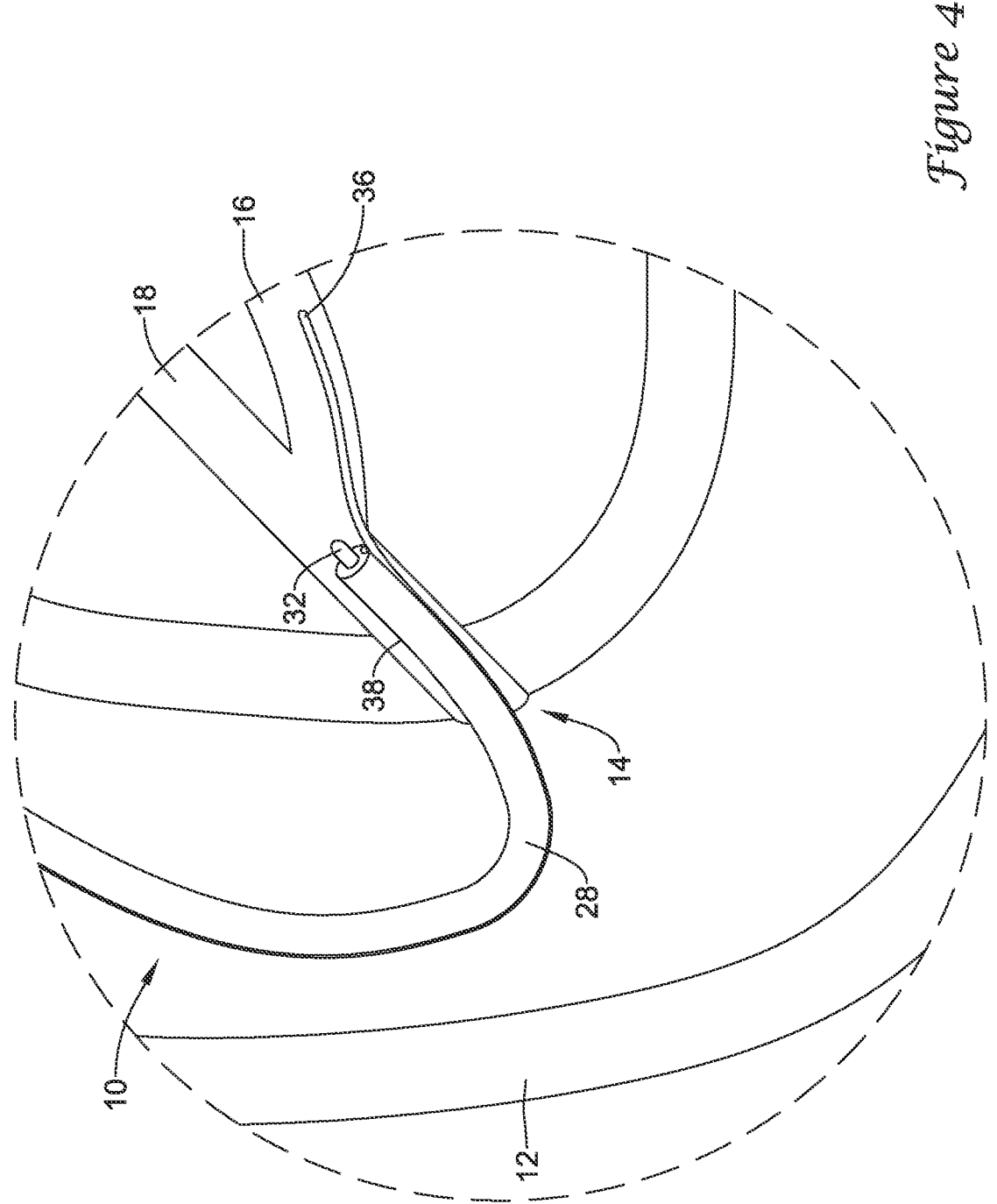

In FIG. 3, catheter system 10 is shown advanced through the ampulla of Vater 14 to a position adjacent when the biliary tree splits into the common bile duct 18 and the pancreatic duct 16. At this point, the clinician may attempt to advance one of the guidewires (e.g., guidewire 36) into the target duct (e.g., in this example the common bile duct 18). If guidewire 36 is successfully advanced into the common bile duct 18, the clinician may continue with the intervention. However, in some instances guidewire 36 may inadvertently end up disposed in the pancreatic duct 16 as shown in FIG. 4. If this is the case, the clinician may choose to remove system 10 from the biliary tree. However, this may require re-cannulation of the ampulla of Vater 14, which can pose technical challenges as well as lead to other complications.

Figure 5:
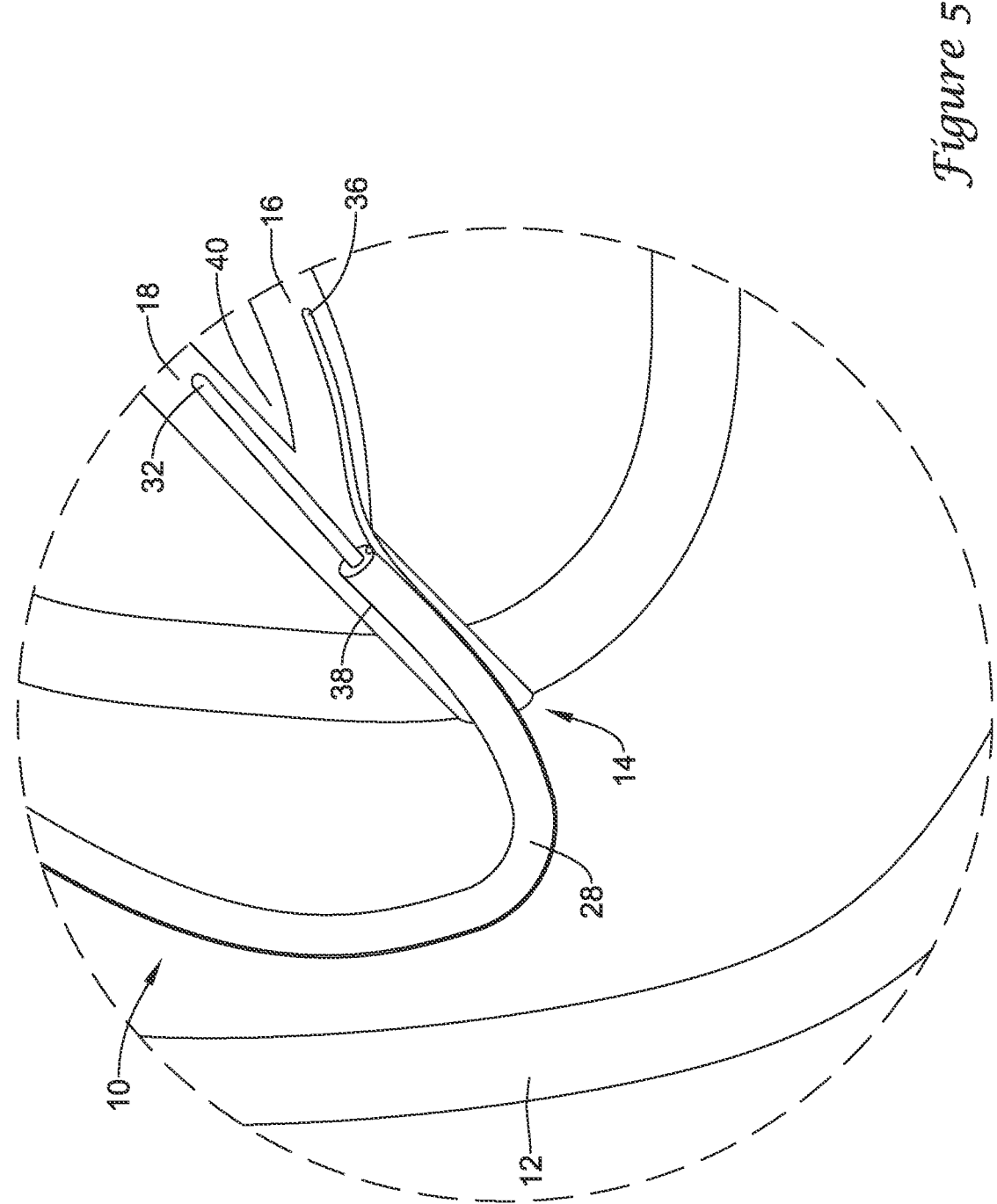
Figure 6:
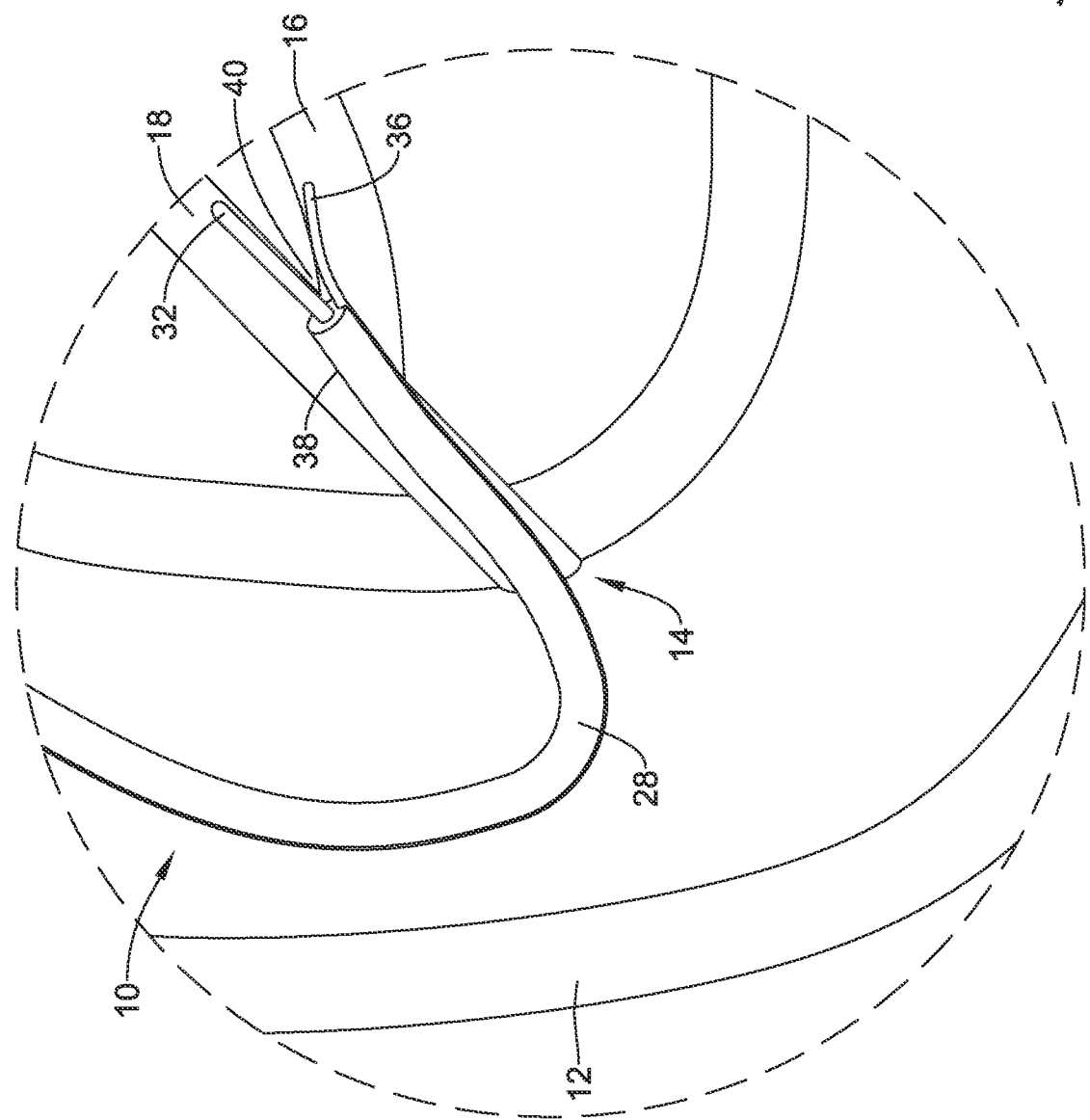
Figure 7:
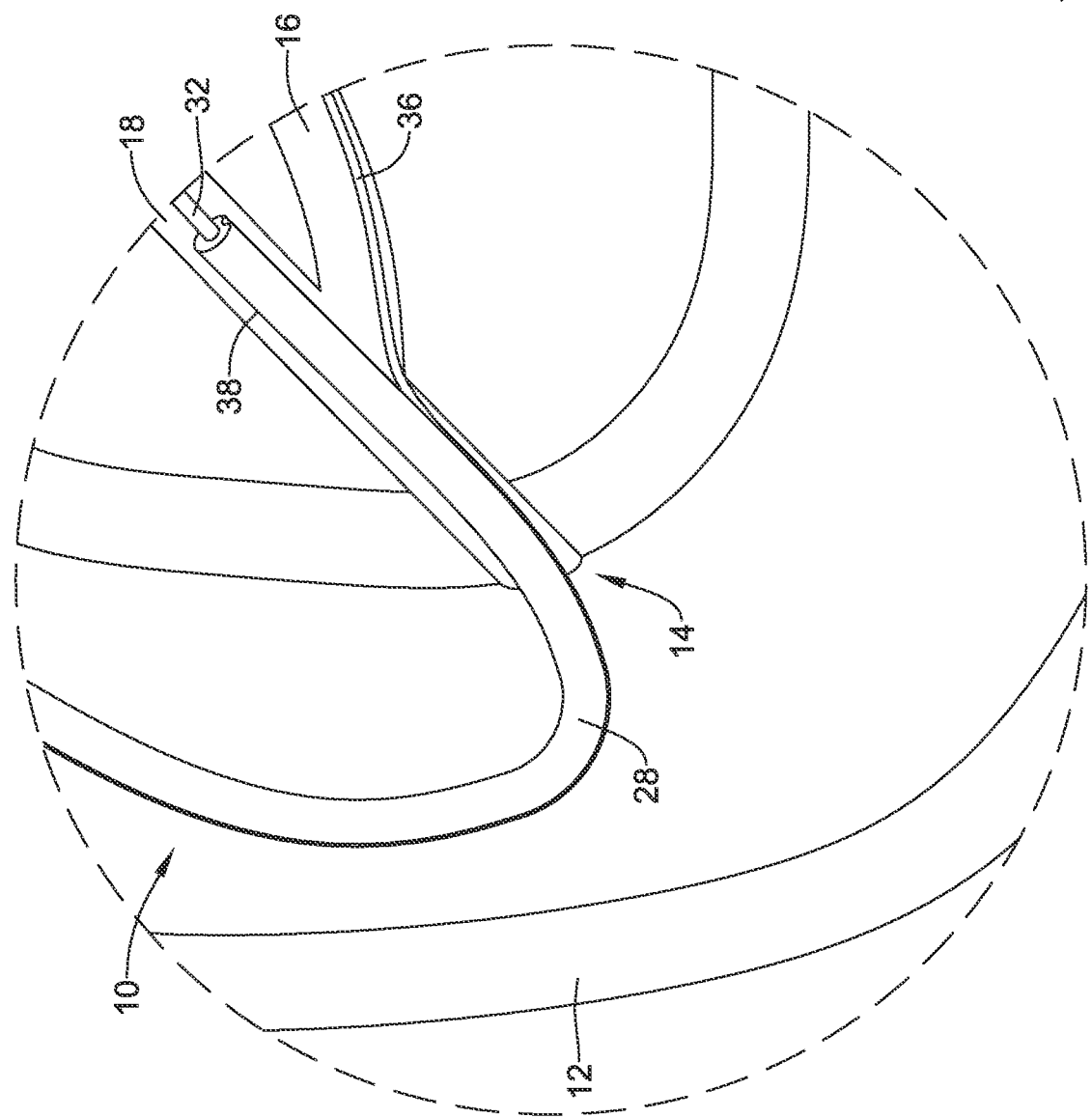

Because system 10 may be a dual-wire access system, the clinician may attempt to access the common bile duct 18 by distally advancing guidewire 32. Because guidewire 36 may at least partially block or otherwise obstruct the pancreatic duct 16, guidewire 36 may more easily access the common bile duct 18 as shown in FIG. 5. With guidewire 32 placed as desired, catheter shaft 38 can be distally advanced over guidewire 32 as shown in FIG. 6. The anatomy 40 adjacent the splitting of the common bile duct 18 and the pancreatic duct 16 may help to "pull" guidewire 36 out of channel 34 as shown in FIG. 7, allowing catheter shaft 38 to reach the target location (e.g., the common bile duct 18). This may also allow another medical device (e.g., a diagnostic or therapeutic catheter including any of those disclosed herein) to be advanced over guidewire 36 (e.g., alongside catheter shaft 28).

With the desired duct now cannulated, the clinician may perform additional treatment step, as appropriate. For example, a treatment catheter may be advanced through catheter shaft 28 (e.g., through lumen 30) and into the desired target. Alternatively, catheter shaft 28 can be removed from the anatomy while leaving guidewire 32 in the target location, and the therapeutic catheter can be advanced over guidewire 32 into the target location. In either case, the form of the therapeutic catheter can vary. In at least some embodiments, the therapeutic catheter can be a sphincterotome, a cutting or tome device, a stent delivery system (e.g., a drainage stent delivery system that may be used to deliver a drainage stent to the biliary and/or pancreatic tree), a needle or biopsy device, or the like, or any other suitable device for accessing or performing a diagnosis or therapy in the biliary and/or pancreatic duct.

In addition, accessing the target location may also incorporate the use of an endoscope. For example, an endoscope may be advanced into a body lumen to a position adjacent to a target location. In at least some embodiments, the target location may be the common bile duct 18 or the pancreatic duct 16. Accordingly, the endoscope may be advanced through the duodenum to a position adjacent to the ampulla of Vater 14. When so positioned, catheter system 10 may be passed through the endoscope toward the desired target. This may include passing catheter shaft 28 through the ampulla of Vater 14.

Figure 8:
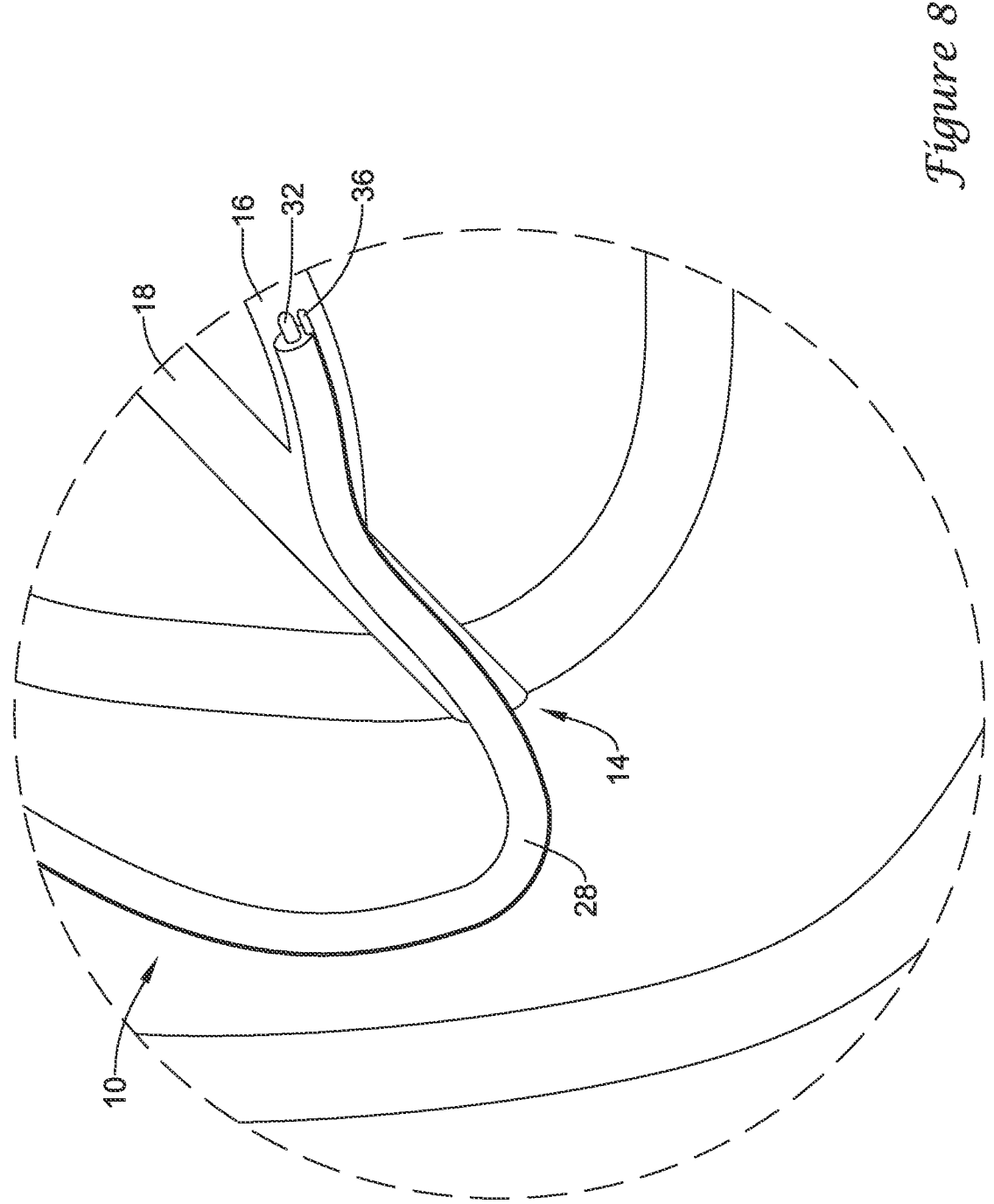
FIG. 8 illustrates part of another example method for using the example catheter system shown in FIG. 2 to access a target duct along the biliary tree.

While the process steps illustrated above may provide a method for accessing a target body lumen, variations are also contemplated to these methods for achieving the same or a similar goal. One example alternative method may include advancing catheter system 10 through a body lumen to a position adjacent where the anatomy splits (e.g., where the common bile duct 18 and the pancreatic duct 16 split). The positioning of system 10 may appear similar to what is shown in FIG. 3. Rather than just advancing guidewire 36 in order to reach a target body lumen (e.g., the common bile duct 18), catheter shaft 28 can be distally advanced as shown in FIG. 8. If catheter shaft 28 successfully reaches the target location, the clinician may proceed with the intervention. However, if catheter shaft 28 is inadvertently placed in a body lumen other than that which was targeted (e.g., the pancreatic duct 16), catheter shaft 28 can be proximally retracted while leaving guidewire 36 in the "undesired" duct (e.g., the pancreatic duct 16). The positioning of system 10 at this point may appear similar to what is shown in FIG. 4. Thereafter, the clinician may proceed as shown in FIGS. 5-7 in order to access the desired body lumen. For example, the clinician may distally advance guidewire 32. Because guidewire 36 may at least partially obstruct the "undesired" body lumen, guidewire 32 may have a greater chance of accessing the target body. Upon successfully accessing the target body lumen (e.g., the common bile duct 18) with guidewire 32, the clinician may proceed with the intervention as appropriate.

Figure 9:
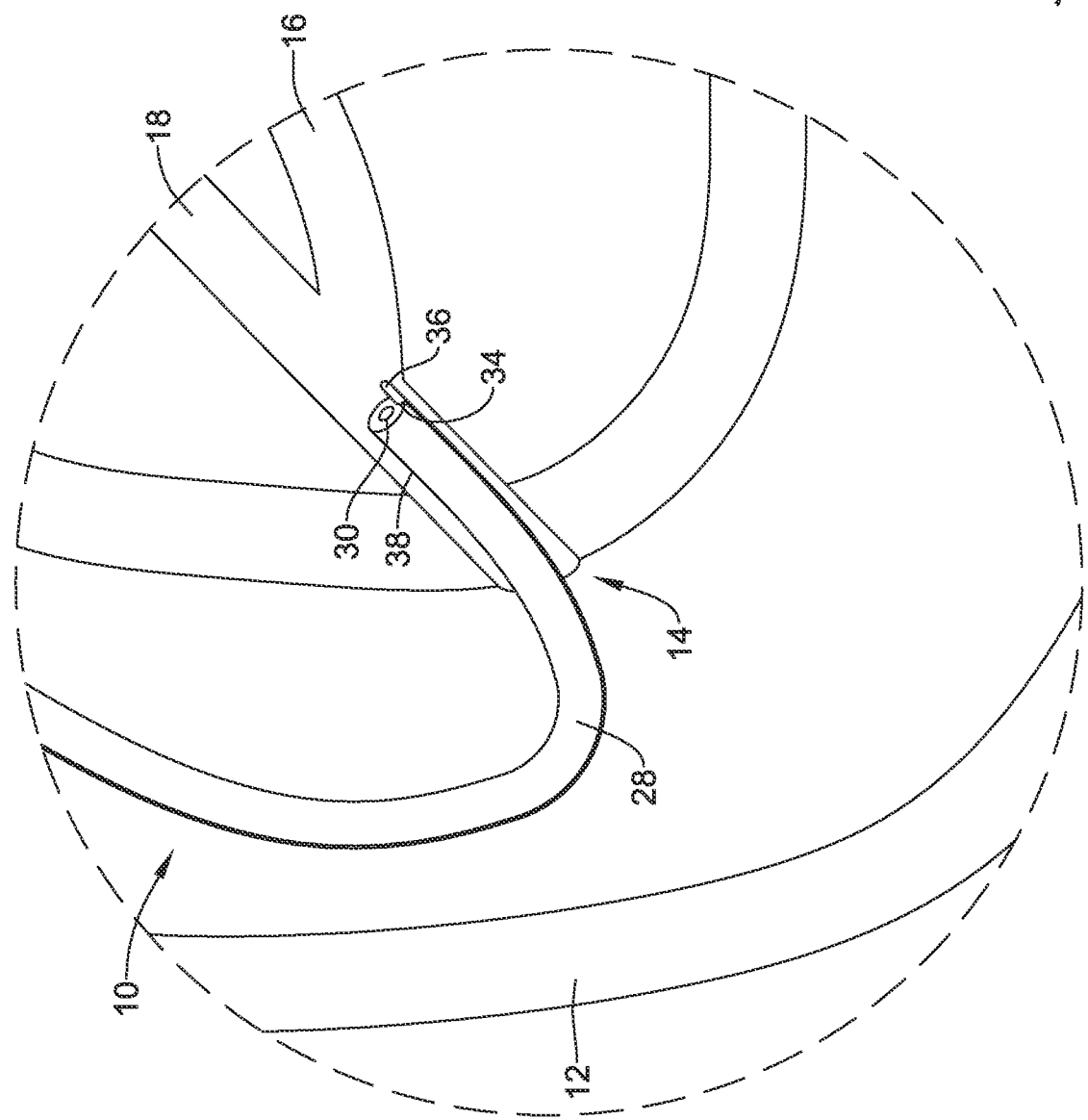
FIGS. 9-10 illustrate part of another example method for using the example catheter system shown in FIG. 2 to access a target duct along the biliary tree.
Figure 10:
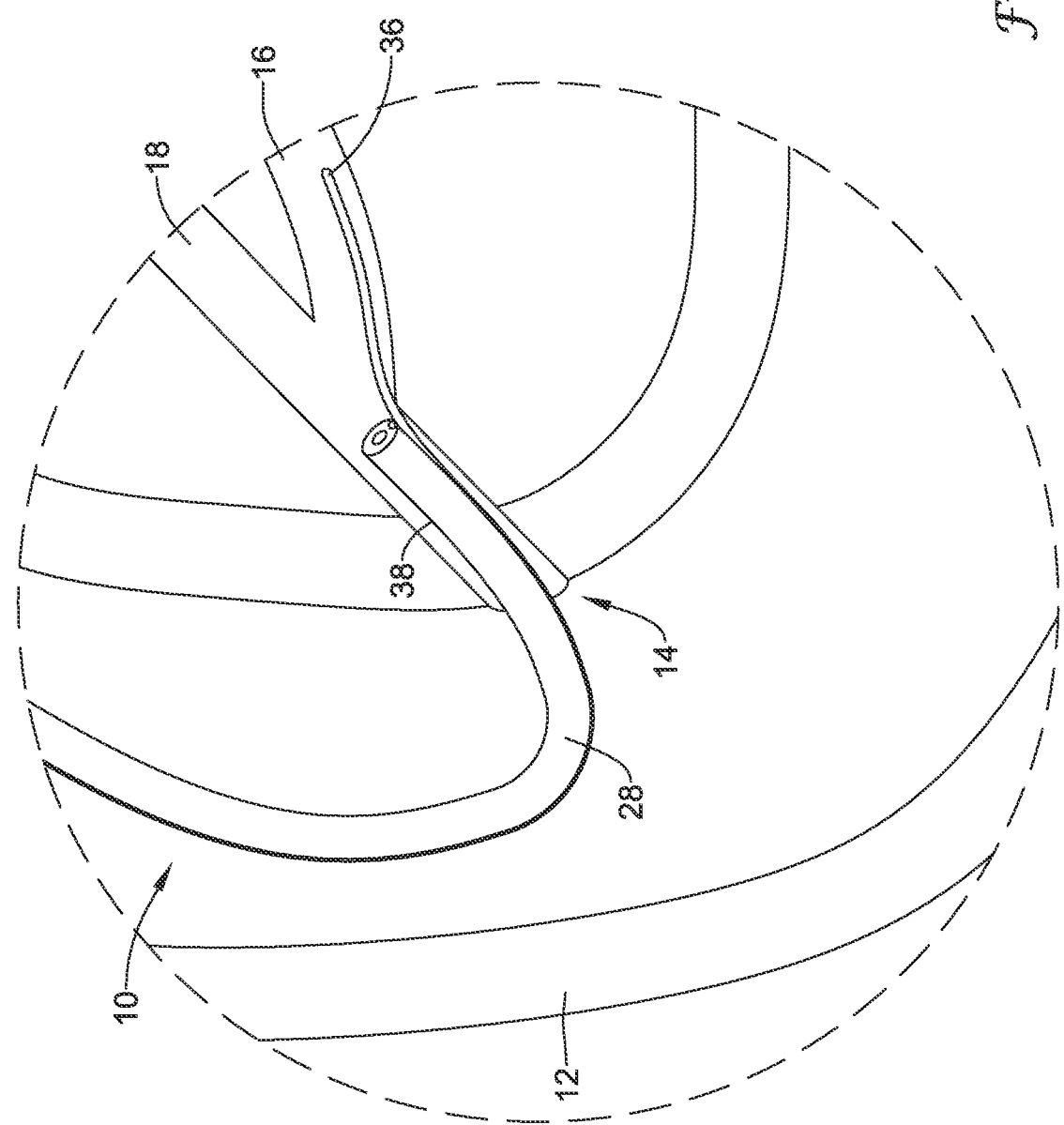

A portion of another alternative method is illustrated in FIGS. 9-10. Here, guidewire 36 may be placed in the anatomy and catheter shaft 28 is advanced over guidewire 36 as shown in FIG. 9. Alternatively, catheter shaft 28 loaded with guidewire 36 may be advanced through the anatomy to a position adjacent to the intended target location. In either case, guidewire 32 is not loaded into catheter shaft 28. Guidewire 36 may be distally advanced to attempt to access a target body lumen as shown in FIG. 10. If guidewire 36 is inadvertently placed in a body lumen other than that which was targeted (e.g., the pancreatic duct 16), guidewire 32 can be advanced through catheter shaft 28 to attempt to access the target body lumen (e.g., the common bile duct 18). The positioning of system 10 at this point may appear similar to what is shown in FIG. 5. Because guidewire 36 may at least partially obstruct the "undesired" body lumen, guidewire 32 may have a greater chance of accessing the target body. Thereafter, the clinician may proceed as shown in FIGS. 6-7 and with the remainder of the intervention, as desired.

The materials that can be used for the various components of system 10 (and/or other systems disclosed herein) may include those commonly associated with medical devices. For simplicity purposes, the following discussion makes reference to system 10 and catheter shaft 28. However, this is not intended to limit the invention as the discussion may be applied to other similar members and/or components of members or systems disclosed herein.

Catheter shaft 28 and/or other components of system 10 may be made from a metal, metal alloy, polymer (some examples of which are disclosed below), a metal-polymer composite, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2-0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties and has essentially no yield point.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of catheter shaft 28 may also be doped with, made of, or otherwise include a radiopaque material including those listed herein or other suitable radiopaque materials.

In some embodiments, a degree of MRI compatibility is imparted into system 10. For example, to enhance compatibility with Magnetic Resonance Imaging (MRI) machines, it may be desirable to make catheter shaft 28 in a manner that would impart a degree of MRI compatibility. For example, catheter shaft 28 or portions thereof may be made of a material that does not substantially distort the image and create substantial artifacts (artifacts are gaps in the image). Certain ferromagnetic materials, for example, may not be suitable because they may create artifacts in an MRI image. Catheter shaft 28 or portions thereof may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Catheter shaft 28 may also include one or more reinforcing structures such as, for example, coils, braids, meshes, or the like. For example, a woven braid may be disposed in the wall of catheter shaft 28. The reinforcing structures may be disposed at essentially any suitable location along the length of catheter shaft 28.

Some examples of suitable polymers that may be used to form catheter shaft 28 and/or other components of system 10 may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6% LCP.

In at least some embodiments, catheter shaft 28 may have a variable stiffness (and/or flexibility) along portions or all of its length. This may include a generally stiffer proximal portion, a flexible body portion, a soft or atraumatic tip. These are just examples.

In some embodiments, the exterior surface of the system 10 may include a coating, for example a lubricious, a hydrophilic, a protective, or other type of coating. Hydrophobic coatings such as fluoropolymers provide a dry lubricity which improves device handling and exchanges. Lubricious coatings improve steerability and improve lesion crossing capability. Suitable lubricious polymers may include silicone and the like, polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, the entire disclosures of which are incorporated herein by reference. Other coatings may be utilized, as desired, to increase surface friction or otherwise add a tacky or adhesive-like (e.g., sticky) feel.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A dual-wire catheter system for accessing a body lumen along the biliary and/or pancreatic tract, the catheter system comprising:
    a catheter shaft having a proximal end, a distal end, a guidewire lumen, and a guidewire channel; and
    a guidewire disposed within the guidewire channel;
    wherein the guidewire lumen extends along a length of the catheter shaft; and
    wherein the guidewire channel is defined in an outer wall of the catheter shaft, the guidewire channel having a distal end proximal of the distal end of the catheter shaft, the distal end of the guidewire channel defining a distal port where the guidewire disposed therein exits the channel, the guidewire channel having a length and being radially open along an entirety of its length, and wherein the guidewire, when disposed within and parallel with the guidewire channel, is configured to extend radially outward of and beyond the catheter shaft along the entire length of the guidewire channel, wherein the guidewire channel distally reduces in depth.

2. The catheter system of claim 1, wherein the guidewire channel is C shaped.

3. The catheter system of claim 1, further comprising a second guidewire channel.

4. The catheter system of claim 3, wherein the second guidewire channel is formed along a length of the catheter shaft outer wall.

5. The catheter system of claim 4, wherein the first and second guidewire channels are C shaped.

6. The catheter system of claim 1, wherein the guidewire lumen extends along a full length of the catheter shaft.

7. The catheter system of claim 1, wherein the guidewire lumen extends centrally along the catheter shaft.

8. The catheter system of claim 1, wherein the guidewire lumen extends along a portion of the catheter shaft and exits through the outer wall at a guidewire port.

9. The catheter system of claim 1, wherein the guidewire channel is defined by a line of weakness in the outer wall of the catheter shaft.

10. The catheter system of claim 1, wherein the guidewire lumen is defined by a tube coupled to the outer wall of the catheter shaft.

11. A dual-wire catheter system for accessing a body lumen along the biliary and/or pancreatic tract, the catheter system comprising:

a catheter shaft having a proximal end, a distal end, an outer wall, and a lumen extending at least partially therebetween;

first and second C-shaped guidewire channels formed along a length of the catheter shaft outer wall, the first and second C-shaped guidewire channels having a length and being radially open along at least a portion of their length, a guidewire disposed within and parallel with the first or second C-shaped guidewire channel, wherein the guidewire is configured to extend radially outward of and beyond the catheter shaft along the length of the first or second C-shaped guidewire channel when the guidewire is disposed within the respective first or second C-shaped guidewire channel, wherein the first and second C-shaped guidewire channels are reduced in depth at a distal end thereof, and the distal end of each guidewire channel is located proximal of the distal end of the catheter shaft.

12. The catheter system of claim 11, wherein the first and second C shaped guidewire channels are radially open along an entirety of their length.

13. The catheter system of claim 11, wherein the lumen extends along a full length of the catheter shaft.

14. The catheter system of claim 11, wherein the lumen extends centrally along the catheter shaft.

15. The catheter system of claim 11, wherein the lumen extends along a portion of the catheter shaft and exits through the outer wall at a guidewire port.

16. The catheter system of claim 11, wherein at least one of the first and second C-shaped guidewire channels is defined by a line of weakness in the outer wall of the catheter shaft.

17. The catheter system of claim 11, wherein the lumen is defined by a tube coupled to the outer wall of the catheter shaft.

18. A dual-wire catheter system for accessing a body lumen along the biliary and/or pancreatic tract, the catheter system comprising:

a catheter shaft having an enclosed guidewire lumen defined therein, and first and second C-shaped guidewire channels extending along at least a portion of a length of the catheter shaft and radially inward of an outer wall of the catheter shaft, the first and second C-shaped guidewire channels each having a length and being radially open along an entirety of its length, a guidewire disposed within and parallel with either of the first or second C-shaped guidewire channel, wherein the guidewire is configured to extend radially outward beyond the outer wall of the catheter shaft along the entire length of the first or second guidewire channel when the guidewire is disposed within the entire length of the respective first or second C-shaped guidewire channel, wherein the radially open first and second C-shaped guidewire channels are reduced in depth at their distal ends, the distal end of each of the first and second C-shaped guidewire channels located proximal of a distal end of the catheter shaft.

* * * * *